United States Patent [19]
Simon et al.

[11] Patent Number: 5,910,612
[45] Date of Patent: Jun. 8, 1999

[54] PREPARATION OF ANHYDROUS 2-AMINO-1-METHOXYPROPANE

[75] Inventors: Joachim Simon, Mannheim; Andreas Henne, Neustadt; Heinz Lingk, Bobenheim-Roxheim, all of Germany

[73] Assignee: BASF Aktiengesellschaft, Ludwigshafen, Germany

[21] Appl. No.: 09/082,543

[22] Filed: May 21, 1998

[51] Int. Cl.⁶ .................................................. C07C 209/02
[52] U.S. Cl. ............................................ 564/497; 564/480
[58] Field of Search ................................... 564/497, 480; 203/14, 75, 77, 78

[56] References Cited

U.S. PATENT DOCUMENTS

| | | |
|---|---|---|
| 3,433,788 | 3/1969 | Somekh et al. .......................... 260/247 |
| 5,074,967 | 12/1991 | Fowlkes . |
| 5,175,369 | 12/1992 | Fowlkes . |

FOREIGN PATENT DOCUMENTS 961174  6/1964  United Kingdom .

*Primary Examiner*—Brian M. Burn
*Attorney, Agent, or Firm*—Keil & Weinkauf

[57] ABSTRACT

The process for preparing anhydrous 2-amino-1-methoxypropane proceeds by (a) admixing a 2-amino-1-methoxypropane-containing water-containing reaction mixture, obtainable from the reaction of 1-methoxy-2-propanol with ammonia on a catalyst, with sodium hydroxide solution, forming an aqueous phase containing sodium hydroxide solution and a 2-amino-1-methoxypropane-containing phase, (b) separating off the 2-amino-1-methoxypropane-containing phase from the aqueous phase and (c) distilling the 2-amino-1-methoxypropane-containing phase, an azeotrope of water and 2-amino-1-methoxypropane, which is recycled to step (a) or (b), first being produced and anhydrous 2-amino-1-methoxypropane then being produced.

9 Claims, No Drawings

PREPARATION OF ANHYDROUS 2-AMINO-1-METHOXYPROPANE

The invention relates to a process for preparing anhydrous 2-amino-1-methoxypropane by separating off water from water-containing reaction mixtures which are obtainable by reacting 1-methoxy-2-propanol with ammonia on a catalyst. 2-Amino-1-methoxypropane is an important intermediate for preparing many chemical compounds.

A variety of processes are known for preparing 2-amino-1-methoxypropane by reacting 1-methoxy-2-propanol with ammonia on catalysts. In each case water-containing reaction mixtures are obtained, from which the water must be removed, in order to obtain anhydrous 2-amino-1-methoxypropane.

U.S. Pat. No. 5,175,369 describes a process of this type, in which 1-methoxy-2-propanol and ammonia are reacted on a fixed bed catalyst. As catalyst, use is generally made of nickel or cobalt catalysts. Diisopropylamine is added to the resulting reaction mixture as entrainer, and a distillation is then carried out. Water and entrainer must then be separated in order to be able to recycle the entrainer to the distillation.

U.S. Pat. No. 5,074,967 describes a process for preparing 2-amino-1-methoxypropane, in which 1-methoxy-2-propanol is reacted with ammonia on a nickel catalyst. The reaction product is subjected to a series of distillation steps. Distillation is initially performed at a specifically set elevated pressure in order to remove a water/2-amino-1-methoxypropane azeotrope and to obtain an anhydrous bottom product. The azeotrope which has been separated off is then distilled at reduced pressure, an azeotrope in turn being obtained which has a substantially lower water content, however. This azeotrope is recycled to the process. In this process, overall yields of less than 65% are obtained.

Both processes are complex and costly to carry out owing to the use of an entrainer or the performance of a multiplicity of distillations under special conditions. In addition, the yields achieved are low.

It is an object of the present invention to provide a process for preparing anhydrous 2-amino-1-methoxypropane from 2-amino-1-methoxypropane-containing water-containing reaction mixtures, which process avoids the disadvantages of the known processes and gives the desired product in a high overall yield.

We have found that this object is achieved according to the invention by a process for preparing anhydrous 2-amino-1-methoxypropane by (a) admixing a 2-amino-1-methoxypropane-containing water-containing reaction mixture, obtainable from the reaction of 1-methoxy-2-propanol with ammonia on a catalyst, with sodium hydroxide solution, forming an aqueous phase containing sodium hydroxide solution and a 2-amino-1-methoxypropane-containing phase, (b) separating off the 2-amino-1-methoxypropane-containing phase from the aqueous phase and (c) distilling the 2-amino-1-methoxypropane-containing phase, an azeotrope of water and 2-amino-1-methoxypropane, which is recycled to step (a) or (b), first being produced and anhydrous 2-amino-1-methoxypropane then being produced.

The invention also relates to a process for separating off water from water-containing reaction mixtures, obtainable from the reaction of 1-methoxy-2-propanol with ammonia, by (a) admixing the reaction mixture with sodium hydroxide solution, forming an aqueous phase containing sodium hydroxide solution and a 2-amino-1-methoxypropane-containing phase, (b) separating off the 2-amino-1-methoxypropane-containing phase from the aqueous phase, with or without (c) distilling the 2-amino-1-methoxypropane-containing phase, an azeotrope of water and 2-amino-1-methoxypropane, which is recycled to step (a) or (b), first being obtained and anhydrous 2-amino-1-methoxypropane then being produced.

According to the invention it has been found that water can be separated off from 2-amino-1-methoxypropane-containing reaction mixtures if the reaction mixture is admixed with sodium hydroxide solution, a two-phase system being formed, and the resulting 2-amino-1-methoxypropane-containing phase is separated off. Generally, the phase separated off is then distilled, in order to obtain anhydrous 2-amino-1-methoxy-1-propane.

Preferably, the abovementioned process steps (a) and (b) are carried out repeatedly, the 2-amino-1-methoxypropane-containing phase obtained in each step (b) being admixed with sodium hydroxide solution in each subsequent step (a). The steps (a) and (b) are preferably carried out until the 2-amino-1-methoxypropane-containing phase ultimately obtained contains at most 5, preferably at most 3, % by weight of water, based on the phase. This can correspond to from 1 to 5 repetitions. Generally, the phase contains from 3 to 5% by weight of water if the steps (a) and (b) are carried out up to 3 times.

Particularly preferably, however, the steps (a) and (b) are carried out continuously, preferably in an extraction column, a centrifugal extractor and/or an extractor cascade. Appropriate apparatuses are known.

In the continuous process procedure, the water-containing reaction mixture and sodium hydroxide solution are passed in counter-current through an extraction column, a centrifugal extractor and/or an extractor cascade. The extractor cascade preferably has from 2 to 5 stages. Suitable extraction columns are, for example, packed columns, sieve-tray columns, cascade columns, pulsed columns, rotary columns and centrifugal columns. The mixer-settler extractor can also be designed so as to save space as a tower extractor or box extractor.

The sodium hydroxide solution used is preferably at least 40% strength, particularly preferably from 45 to 55% strength. With the continuous process also, the water content of the 2-amino-1-methoxypropane-containing phase ultimately obtained is at most 5% by weight of water.

The 2-amino-1-methoxypropane-containing phase obtained from the extraction of steps (a) and (b) is then distilled to purity, the residual water initially passing overhead as an azeotrope with 2-amino-1-methoxypropane. Anhydrous 2-amino-1-methoxypropane then follows. The azeotrope initially obtained is recycled back to step (a) or (b); it is preferably added to the water-containing reaction mixture. The aqueous phase separated off, containing sodium hydroxide solution, is concentrated and the sodium hydroxide solution is recycled back to the process.

The water-containing reaction mixture preferably contains from 10 to 25% by weight, particularly preferably from 15 to 20% by weight, of water, from 70 to 85, particularly preferably from 75 to 83, % by weight of 2-amino-1-methoxypropane, from 0.2 to 5, preferably from 1 to 4, % by weight of 1-methoxy-2-propanol and from 0 to 2, preferably from 0.1 to 1, % by weight of byproducts, the total of the constituents being 100% by weight. 1-Methoxy-2-propanol is preferably reacted to give 2-amino-1-methoxypropane on a catalyst, as described in EP-A-0 394 842 or EP-A-0 696 572. Preferably, use is made of a catalyst of from 40 to 60% by weight of NiO, from 20 to 40% by weight of $ZrO_2$, from 10 to 30% by weight of CuO and from 0 to 2% by weight of $MoO_3$. The reaction is carried out according to the process described in EP-A-0 696 572 under the conditions specified there. Preferably, the pressure is in the range from 21 to 300 bar and the temperature is in the range from 170 to 220° C. Preference is given to continuous reaction in a fixed-bed reactor which is operated, in particular, in the trickle mode. The conversion rate, based on 1-methoxy-2-propanol, is in this case up to 99% at a selectivity for 2-amino-1-methoxypropane of up to 99.5%. The yield of the subsequent distillation is, for example, 87%. This leads to an overall yield of about 86%, as a result of which the process according to the invention gives significantly better yields than the process according to U.S. Pat. No. 5,074,967. The high conversion rate simplifies the work-up to give the anhydrous 2-amino-1-methoxypropane, since only a small amount of starting materials needs to be separated off.

The examples below illustrate the invention.

EXAMPLES

1. Preparation of the catalyst

The catalyst was prepared in accordance with Example 1a) of EP-A-0 394 842. For this purpose, an aqueous solution of nickel nitrate, copper nitrate and zirconium acetate, which contained 4.48% of NiO, 1.52% of CuO and 2.82% of $ZrO_2$, was subjected to simultaneous precipitation at 70° C. in a stirred vessel using a constant stream of 20% strength aqueous sodium carbonate solution, in such a manner that the pH measured by a glass electrode remained constant at 7.0. The resulting suspension was filtered and the filter cake was washed with demineralized water until the electrical conductivity of the filtrate was approximately 20 $\mu$S. Sufficient ammonium heptamolybdate was then incorporated into the still moist filter cake to give the oxide mixture specified below. The filter cake was then dried at 150° C. in a drying cabinet or a spray drier. The hydroxide-carbonate mixture obtained in this manner was then heated at 500° C. for a period of four hours. The resulting catalyst had the composition: 50% NiO, 17% CuO, 1.5% $MoO_3$ and 31.5% $ZrO_2$. The catalyst powder was mixed with 3% graphite and formed into tablets of 6×3 mm. The tablets had a porosity (measured via the water absorption) of 0.20 ml/g and a hardness of 3500 N/cm².

2. Preparation of the crude product

The reaction is performed in a continuous high-pressure reactor. The electrically heated reactor is made of V4A stainless steel and has an internal diameter of 3 cm, with a length of 300 cm. During the reaction, which is carried out in the trickle mode, in addition to ammonia and 1-methoxy-2-propanol, 300 l (S.T.P.)/h of hydrogen are additionally passed through the reactor. Downstream of the reactor, the product is condensed, expanded and discharged in a conventional manner.

700 g of ammonia and 140 g of 1-methoxy-2-propanol are passed per hour at a total pressure of 200 bar and 200° C. through a bed of 500 ml of the catalyst prepared as above under number 1. A product having the following composition is obtained (figures in % of GC peak area, calculated free of ammonia in the anhydrous state):

96.8% 2-amino-1-methoxypropane 2.6% unreacted 1-methoxy-2-propanol 0.6% byproducts The conversion rate of 1-methoxy-2-propanol is 97.4% and the selectivity for 2-amino-1-methoxypropane is 99.4%.

The crude product contains 17% by weight of water.

3. Preparation of pure anhydrous 2-amino-1-methoxypropane 3.5 kg of a crude product having the composition given above under number 2 are first admixed with 0.6 kg of 50% strength sodium hydroxide solution and stirred, for dehydration. The mixture is then allowed to stand and the upper organic phase is separated off. This procedure is repeated two further times, until the water content in the organic phase is still 3 to 5%. The organic phase is then rectified at atmospheric pressure via a packed column having approximately 20 theoretical plates. The column of length 1 m, which is provided with a silvered vacuum jacket, has an internal diameter of 50 mm and is packed with 5 mm V2A stainless steel mesh rings. The distillation procedure is summarized in the table below.

| Fraction | | | Temperature | | | | |
|---|---|---|---|---|---|---|---|
| No. | (g) | (%) | Bottom | Top | RR[1] | $H_2O$[2] | Composition |
| Starting material | 3060 | 100 | | | | 4.6% | 96.8% AMP[3] |
| 1 | 1045 | 34.2 | 96–102° C. | 97–102° C. | 10:1 | 13.4% | 99.8% strength azeotrope AMP/$H_2O$ |
| 2 | 1752 | 57.3 | 102–102° C. | 102° C. | 5:1 | <0.1% | 99.95% AMP, anhydrous |
| Residue | 223 | 7.3 | | | | <0.1% | 28.6% 1-methoxy-2-propanol 63.8% AMP |
| Loss | 40 | 1.2 | | | | | |

[1]Ratio of reflux to take-off
[2]By Karl Fischer
[3]2-Amino-1-methoxypropane

Fraction 1, which principally contains water and 2-amino-1-methoxypropane, is mixed with crude product which is in turn dehydrated with sodium hydroxide solution and distilled. This recycling gives an overall distillation yield of 87%, based on the content of 2-amino-1-methoxypropane in the crude product. The total yield of pure anhydrous 2-amino-1-methoxypropane from synthesis and purification is thus 86% of theory.

Comparative example

A crude output prepared in accordance with U.S. Pat. No. 5,074,967 by hydrogenating amination of 1-methoxy-2-propanol with ammonia has the following composition (% of GC peak areas, calculated free of ammonia in the anhydrous state):

67% 2-amino-1-methoxypropane

30% 1-methoxy-2-propanol

3 % byproducts

The conversion rate of 1-methoxy-2-propanol is 70% and the selectivity for 2-amino-1-methoxypropane is 96%. The crude product contains 12% by weight of water. The multistage pressure distillation described in U.S. Pat. No. 5,074,967 gives a distillation yield of 90% in the secondary processing. This gives the total yield of anhydrous 2-amino-1-methoxypropane in this process at 61% of theory.

We claim:

1. A process for preparing anhydrous 2-amino-1-methoxypropane by
   (a) admixing a 2-amino-1-methoxypropane-containing water-containing reaction mixture, obtained from the reaction of 1-methoxy-2-propanol with ammonia on a catalyst, with sodium hydroxide solution, forming an aqueous phase containing sodium hydroxide solution and a 2-amino-1-methoxypropane-containing phase,
   (b) separating off the 2-amino-1-methoxypropane-containing phase from the aqueous phase and
   (c) distilling the 2-amino-1-methoxypropane-containing phase, an azeotrope of water and 2-amino-1-methoxypropane, which is recycled to step (a) or (b), first being produced and anhydrous 2-amino-1-methoxypropane then being produced.

2. A process for separating off water from water-containing reaction mixtures, obtained from the reaction of 1-methoxy-2-propanol with ammonia, by
   (a) admixing the reaction mixture with sodium hydroxide solution, forming an aqueous phase containing sodium hydroxide solution and a 2-amino-1-methoxypropane-containing phase,
   (b) separating off the 2-amino-1-methoxypropane-containing phase from the aqueous phase, with or without
   (c) distilling the 2-amino-1-methoxypropane-containing phase, an azeotrope of water and 2-amino-1-methoxypropane, which is 5 recycled to step (a) or (b), first being obtained and anhydrous 2-amino-1-methoxypropane then being produced.

3. A process as claimed in claim 1, wherein the steps (a) and (b) are carried out repeatedly, the 2-amino-1-methoxypropane-containing phase obtained in each step (b) being admixed with sodium hydroxide solution in each subsequent step (a).

4. A process as claimed in claim 1, wherein the steps (a) and (b) are carried out continuously.

5. A process as claimed in claim 4, wherein the steps (a) and (b) are carried out in an extraction column, a centrifugal extractor and/or an extractor cascade.

6. A process as claimed in claim 3, wherein the 2-amino-1-methoxypropane-containing phase used in step (c) contains at most 5% by weight of water, based on the phase used.

7. A process as claimed in claim 1, wherein the water-containing reaction mixture contains from 10 to 25% by weight of water, from 70 to 85% by weight of 2-amino-1-methoxypropane, from 0.2 to 5% by weight of 1-methoxy-2-propanol and from 0 to 2% by weight of byproducts, the total of the constituents being 100% by weight.

8. A process as claimed in claim 1, wherein the water-containing reaction mixture is prepared by reacting 1-methoxy-2-propanol with ammonia, the reaction having one or more of the features below:
   pressure in the range from 21 to 300 bar;
   temperature in the range from 170 to 220° C.;
   continuous reaction on a fixed-bed catalyst;
   reaction in the trickle mode;
   catalyst of from 40 to 60% by weight of NiO, from 20 to 40% by weight of $ZrO_2$, from 10 to 30% by weight of CuO and from 0 to 2% by weight of $MoO_3$, the total amount being 100% by weight.

9. A process as claimed in claim 1, wherein the sodium hydroxide solution used is at least 40% strength.

* * * * *

UNITED STATES PATENT AND TRADEMARK OFFICE
CERTIFICATE OF CORRECTION

PATENT NO.: 5,910,612

DATED: June 8, 1999

INVENTOR(S): SIMON et al.

It is certified that error appears in the above-identified patent and that said Letters Patent is hereby corrected as shown below:

On the front page of the patent, insert the following priority information:

--[30]   Foreign Application Priority Data

May 30, 1997   [DE]   Germany ................ 197 22 700.7.--

Signed and Sealed this

Nineteenth Day of October, 1999

*Attest:*

Q. TODD DICKINSON

*Attesting Officer*          Acting Commissioner of Patents and Trademarks